United States Patent [19]

Alvarez

[11] 4,139,009
[45] Feb. 13, 1979

[54] HYPODERMIC NEEDLE ASSEMBLY WITH RETRACTABLE NEEDLE COVER

[76] Inventor: Marcial Alvarez, 225 E. Jersey St., Elizabeth, N.J. 07206

[21] Appl. No.: 836,977

[22] Filed: Sep. 27, 1977

Related U.S. Application Data

[63] Continuation-in-part of Ser. No. 744,405, Nov. 23, 1976, abandoned.

[51] Int. Cl.² ............................................. A61M 5/00
[52] U.S. Cl. ............................... 128/218 N; 128/221
[58] Field of Search ............. 128/218 N, 218 R, 221, 128/215, 272.3, 243, 347, 216, 214.4

[56] References Cited

U.S. PATENT DOCUMENTS

| | | | |
|---|---|---|---|
| 2,072,346 | 3/1937 | Smith | 128/347 X |
| 2,711,732 | 6/1955 | Solomon | 128/215 |
| 3,517,128 | 6/1970 | Hines | 128/243 X |
| 3,840,008 | 10/1974 | Noiles | 128/214.4 |

FOREIGN PATENT DOCUMENTS 9700 of 1902 United Kingdom ................ 128/218 N

*Primary Examiner*—John D. Yasko
*Attorney, Agent, or Firm*—Weingram & Klauber

[57] ABSTRACT

A disposable hypodermic needle assembly is disclosed which includes a permanently attached but retractable covering means for the forward portions of the needle. The assembly comprises a hub portion adapted for attachment to the outlet end of a syringe, the hub portion including a central passageway for enabling liquid flow to or from the syringe. A hollow needle is connected to the hub with its inlet end communicating with the central passageway of the hub. An annular slide member surrounds and is longitudinally slideable with respect to the needle, the member being positionable to normally cover the forward portion of the needle. A plurality of elastically resilient arms extend between the hub portion and slide member. The said arms, which may e.g. comprise plastic strips, act to normally maintain the slide member in its position covering the forward portion of the needle. The arms are bowable away from the longitudinal axis of the needle upon the slide member being urged toward the hub portion by contact of the slide member with the skin of a patient during injection of the needle. The outward bowing of the elastically resilient arms generate a restoring force urging the slide member back over the forward needle portion upon withdrawal of the assembly from contact with the skin. The assembly may also include a slideable locking ring member, which in one position embraces and constrains the arms, to thereby lock the slide member against rearward movement.

10 Claims, 6 Drawing Figures

U.S. Patent
Feb. 13, 1979
4,139,009
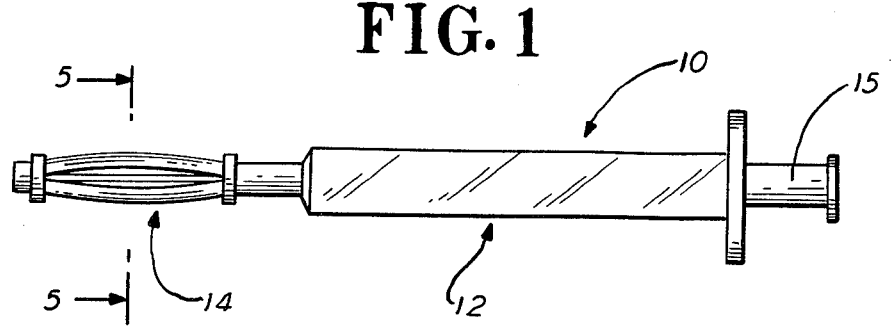
FIG. 1
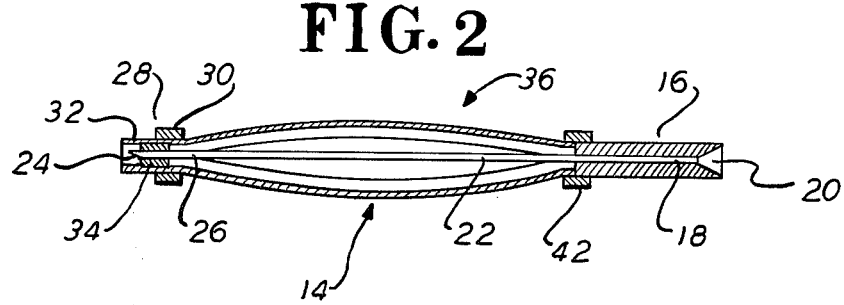
FIG. 2
FIG. 4
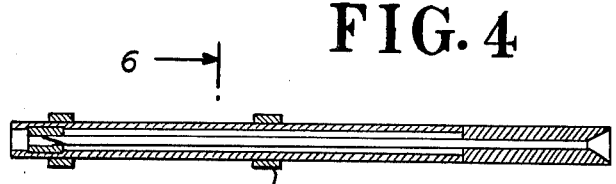
FIG. 3
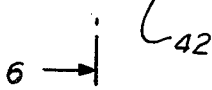
FIG. 5
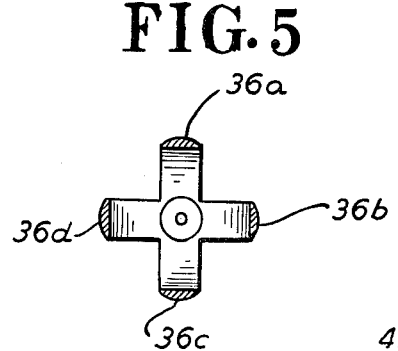
FIG. 6
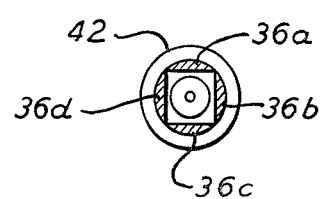

4,139,009

HYPODERMIC NEEDLE ASSEMBLY WITH RETRACTABLE NEEDLE COVER

BACKGROUND OF INVENTION

This application is a continuation-in-part of my co-pending application Ser. No. 744,405, filed Nov. 23, 1976, and entitled "RETRACTILE PERMANENT HYPODERMIC NEEDLE COVER" now abandoned.

This invention relates generally to hypodermic syringe apparatus, and more specifically relates to a disposable hypodermic needle assembly, which includes a permanently attached but retractable covering means for the forward portion of the needle.

Within recent years hypodermic apparatus have become widely available in the form of disposable devices, consisting in many instances of a syringe in association with a hypodermic needle assembly. The said needle assembly typically includes the usual hollow needle, together with connecting means such as a hub assembly or the like, which enables fluid-tight connection of the needle to the syringe outlet. The entire syringe and needle assembly may be sealed as a unit into a package or envelope which is opened at the time the device is to be used, at which time the device is removed in a relatively sterile condition.

In common devices of the foregoing type, the needle assembly often includes a simple cylindrical cover, the open end of which frictionally engages with and is held by the hub portion. This cover is removed prior to use of the hypodermic apparatus, after which the device is filled in the usual manner by the medical practitioner, and then utilized to effect the required injection. In general, it is then contemplated that the used device will be discarded, i.e. the unit as mentioned is deemed disposable.

In disposable devices of the aforementioned type, it has unfortunately been repeatedly found that once the practitioner removes the needle cover, the cover is placed to one side, i.e. the cover is indeed a completely separable element from the remaining portions of the apparatus. Upon completion of the patient injection the then uncovered hypodermic device, rather than being immediately discarded, is more often than not placed on a table or other convenient surface while the practitioner attends to the patient. In such condition the uncovered device constitutes a serious hazard, i.e. it continues to lie at a point whereat an individual may inadvertently be injured by the exposed needle. In the event the used needle makes contact in this manner with a patient or medical attendant, not only is the danger of injury high, but moreover since the needle has been utilized in injection of a patient, it may readily be contaminated with organisms which can effect disease transfer to the individual making contact with same. A specific danger, of course, is the well recognized possibility for thus transmitting serum hepatitis.

From time to time proposals have been made for providing disposable hypodermic devices of the aforementioned type with a needle assembly including a covering element which is permanent in nature but retractable. The objective of a construction of this type is partially one of assuring that the cover remains with the needle assembly, so that there may be increased assurance that the cover will be replaced subsequent to use of the device. An example of this type of device may be seen e.g. in U.S. Pat. No. 3,134,380.

While, therefore, the advantages of a retractable cover construction have been appreciated in the prior art, observation will establish that such devices as have been proposed have achieved little degree of commercial acceptance. While a number of reasons may be advanced for this failure of such devices to reach an apparently waiting market, it would appear that the complexity and comparatively high cost of prior constructions has been a major deterrent to their use. Such prior constructions have thus not only incorporated in many instances complex and costly elements, but have in other instances been deemed impractical. For example, in some instances the prior structures are incompatible with expeditious filling of the syringe from the standard type of vial utilized by medical practioners. In other instances the retractability is simply of insufficient efficiency and dependability — i.e. there is no clear assurance that the used needle assembly will be restored to a covered configuration, and will remain in that condition.

Pursuant to the foregoing, it may be regarded as an object of the present invention, to provide a disposable hypodermic needle assembly for use in hypodermic apparatus, which assembly includes a permanent but retractable covering for the discharge portion of the needle; and which assembly is so constructed as to operate in a simple but highly effective fashion.

It is a yet further object of the present invention, to provide apparatus of the foregoing type which includes simple features enabling positive locking of the needle covering portion of the apparatus.

It is a still further object of the invention, to provide a disposable hypodermic needle assembly utilizable with conventional syringes or the like, which assembly is readily adapted for use by relatively inexperienced medical practitioners, nursing personnel or the like; which device further, by virtue of its construction tends to reduce psychological apprehension experienced by a patient during injection of medications.

SUMMARY OF INVENTION

Now in accordance with the present invention, the foregoing objects, and others as will become apparent in the course of the ensuing specification, are achieved in a disposable hypodermic needle assembly which includes a permanently attached but retractable covering means for the forward portions of the needle. The assembly, which is utilizable with conventional syringes including those of the disposable type, comprises a hub portion adapted for attachment to the outlet end of the syringe. The hub portion includes a central passageway for enabling liquid flow from the syringe. A hollow needle is connected to the hub with its inlet end communicating with the central passageway through the hub. An annular slide member surrounds and is longitudinally slideable with respect to the needle, the member being positionable to normally cover the forward portion of the needle.

A plurality of elastically resilient arms extend between the hub portion and slide member. The said arms which may, e.g. comprise plastic strips, act to normally maintain the slide member in its position covering the forward portion of the needle. The arms are bowable away from the longitudinal axis of the needle upon the slide member being urged toward the hub portion by contact of the said member with the skin of the patient during injection of the needle. The outward bowing of the elastically resilient arms generate a restoring force urging the slide member back over the forward needle portion upon withdrawal of the assembly from skin contact.

An annular locking ring member may further be provided, which member is slideable between a first longitudinal position adjoining and at least partially surrounding the hub portion, whereat the said member does not interfere with operation of the needle assembly, and a second position approximately midway between the hub means and the normal position of the slide means. In the second position the locking ring member surrounds and embraces the resilient arms. This brings the adjacent arms into side-to-side contact, thereby covering and protecting the needle, and acts further to restrain outward bowing of the arms. This action effectively locks the slide member against rearward movement, thereby preventing (in positive fashion) uncovering of the forward tip of the needle.

BRIEF DESCRIPTION OF DRAWINGS

The invention is diagrammatically illustrated, by way of example, in the drawings appended hereto in which:

FIG. 1 is a side elevational view of apparatus in accordance with the present invention, the said apparatus being shown in conjunction with a conventional hypodermic syringe;

FIG. 2 is a longitudinal cross-sectional view through the hypodermic needle assembly portion of the FIG. 1 depiction;

FIG. 3 is a schematic view depicting the apparatus of the present invention in the course of the syringe being filled with an injecting medication;

FIG. 4 is a longitudinal cross-sectional view similar to FIG. 2, but showing the locking ring member emplaced to effect locking action;

FIG. 5 is a transverse cross-sectional view through the needle assembly of the present invention, the said view being taken along the line 5—5 of FIG. 1; and FIG. 6 is a transverse cross-sectional view similar to FIG. 5, but taken along the line 6—6 of FIG. 4.

DESCRIPTION OF PREFERRED EMBODIMENT

In FIG. 1 herein a hypodermic device 10 is shown, including features of the present invention. Device 10 includes a syringe 12, of generally conventional construction, to which is removably adjoined a hypodermic needle assembly 14 in accordance with the principles of the invention.

Per se the syringe 12 is a conventional device, and assembly 14, with such modifications as may be required to effect an appropriate interfit, can be utilized with a variety of such syringes. For purposes of concretely illustrating the present invention, however, it may be considered that syringe 12 is of a disposable plastic type, i.e. formed of such plastics as polyethylene, polyvinyl chloride (PVC), or the like. The entire device 10 will typically be provided to the consumer, i.e. the medical practitioner, in a sealed envelope or other package, so that the device when removed from said package is in a completely sterile condition. Since the syringe 12 is, as indicated, conventional, details of this particular device are not set forth herein.

As may be seen from conjunctive study of FIGS. 1, 2, and the cross-sectional view of FIG. 5, the needle assembly 14 comprises at its rearward end a hub portion 16, again formed of suitable plastics or the like. Hub portion 16 carries a central passageway 18, which passageway connects to a flared opening 20 at the rearward end of portion 16. Passageway 20 is adapted to engage the tip, i.e. the outlet of the syringe 12, with the specific configuration of the opening being subject to change to adapt to various types of syringes. A conventional hollow needle 22 is mounted with its rearward i.e. inlet end, inserted into passageway 18, so as to enable flow through tip 24 of the needle upon the operator manipulating the piston 15 of syringe 12 — i.e. during filling of the syringe or during a patient injection.

Spaced from hub member 16, i.e. toward the forward portion 26 of needle 22, is an annular slide member 28. Such member comprises an outer ring 30 of somewhat enlarged proportions, an inner ring 32, and a sleeve 34 within the inner ring 32. These three elements can be separately formed and secured together by conventional joining operations; for example, both outer ring 30 and inner ring 32 can comprise a molded plastic, such as polyethylene or polytetrafluoroethylene (PTFE), etc. Sleeve 24, since it engages in slideable fashion needle 22, preferably should have some lubricating qualities, and hence can either comprise a plastic having these qualities such as a PFTE, or can comprise a very smooth metal such as stainless steel or the like. It is also within the realm of the invention for the entire slide member 28 to comprise a single molding of plastic or the like.

In any of these events it is seen that the slide member 28 surrounds the said needle 22 and is longitudinally slideable with respect hereto; i.e. more specifically the slide member 28 is capable of rearward movement to thereby uncover the forward portions 26 of the needle, including tip 24 during an injection operation.

Slide member 28 is seen to be connected to hub member 16 by means of a plurality of arms 36. Arms 36 comprise an elastically resilient, flexible material, such as the plastics previously referred to. As best seen in FIG. 5 there are preferably four such arms, i.e. arms 36a, 36b, 36c and 36d, although the actual number of such arms can be somewhat higher or lower.

The arms are attached at their opposed ends to slide member 28 and to hub portion 16. Such attachment can be effected by any conventional joining operation; once again it is within the province of the invention for such arms to be molded integrally — not only with slide member 28, but also with hub portion 16. Each of the arms 36a, 36b, 36c and 36d are in their "normal" unstressed conditions, slightly bowed away from the longitudinal needle axis at points between their attached ends. Thus such arms are respectively spaced from adjacent arms at longitudinal points between slide member 28 and hub portion 16.

As best seen in FIGS. 1 and 2, the construction set forth is such that the normal configuration of the assembly 14 is such that arms 36 are bowed slightly outwardly, i.e. in their unstressed condition arms 36 bow away slightly from the longitudinal axis of needle 22, to thereby, in the absence of any applied force, normally maintain slide member 28 in the position shown in FIGS. 1 and 2. Such member in its normal position therefore covers the forward portion 26 of the needle, and specifically covers the outlet or tip 24 thereof. Since the forward portions of the needle are thus covered in this normal position, the needle tip 24 and adjacent portions are fully protected — both from contamination and from possible physical damage — until such time as device 10 is to be used in effecting an injection.

When the present device is to be utilized, and as best seen in FIG. 3, it is only necessary for the operator to bring the entire device 10 including assembly 14 into contact with the outlet end of a vial 38 containing the solution or other medicament 40 which is to fill the syringe 12. The operator then exerts a slight amount of forward pressure, which causes needle 22 to enter vial 38. This simultaneously of course causes slide number 28 to retract axially along the needle 22, i.e. to slide rearwardly toward hub 16. As this occurs, and as seen in FIG. 5, the flexible resilient arms 36 bow outwardly in the more pronounced fashion shown. This distortion of arms 36, in turn generates a restoring force, i.e. tending to restore slide member 28 to its normal position. In consequence, upon withdrawal of assembly 14 from vial 38, the configuration of FIG. 2 is restored, at which point device 10 is ready for the patient injection.

In this last connection, it will of course be appreciated that the action just described, i.e. the mechanical retraction of slide member 28 with generation of restoring forces by virtue of distortion of arms 36, occurs in precisely similar fashion upon the device 10 being used to effect the patient injection. Thus one can regard the foregoing description of filling of syringe 12, i.e. the mechanical action described, as being precisely the action occurring upon patient injection; i.e. in this latter instance contact with the skin surface of the patient cause the elastic retraction of member 28. In turn, once the device is withdrawn from the patient, i.e. the injection completed, the assembly 14 will be restored to its normal configuration of FIG. 2.

As best seen from FIGS. 2 and 4, the present assembly 14 includes a further feature of considerable significance in preventing accidental injury or misuse of the present device. In particular it is seen that an annular locking ring 42 is provided, which ring has an integral diameter such that it may in a first position (FIG. 2) surround the forward portion of hub member 16. Member 42 is longitudinally slideable with respect to the present assembly, but in the said first position shown in FIG. 2, it is completely clear of interference with the bowing action of arms 36 which has previously been described, i.e. the outward bowing of arms 36 which occurs upon retraction of slide member 28.

As shown in FIG. 4 however, the locking ring 42 may be moved forwardly as desired. As the ring 42 is thus moved forwardly, it surrounds and embraces the arms 36; and upon it reaching a position as shown in FIG. 4, i.e. approximately midway between hub means 16 and slide member 28, it is seen that arms 36 are constrained or pinched inwardly. Two results obtain from this action: Firstly, and as may be seen from FIGS. 4 and 6, the arms 36a, 36b, 36c, and 36d are brought into lateral side-to-side contact, whereby they cover and protect all portions of needle 22. Secondly, with the ring 42 in this FIG. 4 position, the force then required to move slide member 28 rearwardly is so great, that for all practical purposes slide member 28 is locked in its "normal" position.

In a typical operation of device 10 the locking member 42 will be in the locking position when device 10 is removed from its package, and will again be so positioned upon completion of the patient injection. Once the slide member is placed in the position shown in FIG. 4, as mentioned, it is virtually impossible to accidentally uncover the tip 24 of needle 22, and hence all danger of accidental contact or injury with the needle 22, which at this point is no longer sterile, is achieved.

The present invention, in addition to providing advantages of safety and sterility afforded by use of the retractable needle covering slide member, has other significant advantages from a medical viewpoint. One of these, for example, is the considerable psychological improvement which is yielded from the viewpoint of the patient. Thus it is appreciated by those familiar with the medical arts, that most patients, including especially children, have considerable apprehension of a hypodermic apparatus, which largely arises from viewing of the needle portion of same. In the present device the forward portions of the needle are completely covered from view up and until the time that the needle is actually engaged with the skin.

A further advantage in that connection is that the arrangement permits a relatively unskilled individual to utilize a hypodermic apparatus incorporating the invention, since it is possible with the invention to place the device 10 in direct contact with the skin just before the actual injection is effected. This enables accurate positioning, and also introduces a degree of anesthesia which occurs by virtue of the pressure generated by skin contact with the forward-facing end of slide member 28. The present invention by virtue of these advantages is especially well-suited to self-injection, e.g. by diabetic patients or so forth.

While the present invention has been particularly set forth in terms of specific embodiments thereof, it will be understood in view of the instant disclosure, that numerous variations upon the invention are now enabled to those skilled in the art, which variations yet reside within the scope of the present teaching. Accordingly the invention is to be broadly construed, and limited only by the scope and spirit of the claims now appended hereto.

I claim:

1. A disposable hypodermic needle assembly, including a permanently attached but retractable covering means for the forward portions of the needle; said assembly comprising in combination:
    a hub portion adapted for attachment to the outlet end of a syringe, said portion including a central passageway for enabling liquid flow to or from the outlet of said syringe;
    a hollow needle connected to said hub with the inlet end thereof communicating with the central passagwway of said hub;
    an annular slide member surrounding said needle and being longitudinally slideable with respect thereto, said member being positionable to normally cover the said forward portion of said needle; and
    a plurality of elastically resilient arms extending between said hub portion and said slide member, said arms in their unstressed condition normally maintaining said slide member in said position covering the forward portion of said needle; said arms being elastically bowable away from the longitudinal axis of said needle upon said slide member being urged toward said hub portion by contact of said slide member with the skin of a patient during injection of said needle beneath said skin; the bowing of said arms away from said longitudinal needle axis generating a restoring force for urging said slide member back over said needle forward portion upon withdrawal of said assembly from contact with said skin.

2. An assembly in accordance with claim 1, wherein said resilient arms are attached at their opposed ends to said hub portion and slide member, and wherein said arms in their said unstressed condition are slightly bowed away from the longitudinal needle axis at points between their attached ends, whereby said arms are mutually spaced with respect to one another between said points of attachment.

3. An assembly in accordance with claim 2, wherein said arms comprise plastic strips.

4. An assembly in accordance with claim 3, wherein said strips are four in number, and are spaced 90° with respect to one another about said needle.

5. An assembly in accordance with claim 2, further including an annular locking ring member, said member surrounding said arms and being slideable with respect to same between a first position adjoining said hub portion whereat said member is free from interference with operation of said assembly, and a second position between said hub means and said normal position of said slide means, whereat said locking ring member surrounds and embraces said resilient arms to restrain outward bowing of said arms, thereby locking said slide member against rearward movement toward said hub portion.

6. A disposable hypodermic apparatus, including a permanently attached but retractable covering means for the forward tip of the needle thereof; said apparatus comprising:
 a disposable syringe including an outlet for a liquid to be injected therefrom;
 a hub portion adapted for attachment to the outlet end of said syringe, said portion including a central passageway for enabling liquid flow from the syringe outlet;
 a hollow needle connected to said hub portion, with the inlet end thereof communicating with the central hub passageway;
 a slide member surrounding said needle and being longitudinally slideable with respect therero, said member being positionable to normally cover the said forward tip of said needle; and
 a plurality of elastically resilient arms being attached to and extending between said hub portion and slide member, said arms in their unstressed condition acting to normally maintain said slide member in said position covering the forward tip of said needle; said arms being elastically bowable away from the needle axis upon said slide member being urged toward said hub portion by contact of said slide member with the skin of a patient during injection of said needle; the elastic bowing of said arms generating a restoring force urging said slide member to return to said normal position upon withdrawal of said apparatus from contact with said skin.

7. Apparatus in accordance with claim 6, wherein said resilient arms in their said unstressed condition are slightly bowed away from the longitudinal needle axis at points between their attached ends, whereby said arms are mutually spaced between said points of attachment.

8. Apparatus in accordance with claim 7, wherein said arms comprise a resilient plastic.

9. Apparatus in accordance with claim 8, wherein said arms are four in number, and are spaced 90° with respect to one another about said needle axis.

10. Apparatus in accordance with claim 7, further including a locking member positionable to surround said arms at an axial position approximately midway between said slide member and said hub portion, said member acting at said position to constrain said arms against outward bowing, thereby placing said arms in side-to-side contact to cover and protect lateral portions of said needle, and said constraint further preventing retraction of said slide member to uncover said needle tip.

* * * * *